United States Patent
Hazin et al.

(10) Patent No.: US 10,618,038 B2
(45) Date of Patent: Apr. 14, 2020

(54) FUNCTIONALIZED BORON NITRIDE CATALYSTS FOR THE PRODUCTION OF LIGHT OLEFINS FROM ALKANE FEEDS VIA OXIDATIVE DEHYDROGENATION

(71) Applicant: SABIC Global Technologies B.V., Bergen op Zoom (NL)

(72) Inventors: Paulette N. Hazin, Sugar Light, TX (US); Zhun Zhao, Houston, TX (US); Ashwin Patel, Friendswood, TX (US); Jason Loiland, Houston, TX (US); Dick Alan Nagaki, The Woodlands, TX (US)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 16/046,665

(22) Filed: Jul. 26, 2018

(65) Prior Publication Data

US 2020/0030781 A1    Jan. 30, 2020

(51) Int. Cl.
*B01J 21/02* (2006.01)
*B01J 27/24* (2006.01)
(Continued)

(52) U.S. Cl.
CPC .............. *B01J 27/24* (2013.01); *B01J 23/02* (2013.01); *B01J 23/10* (2013.01); *B01J 23/14* (2013.01);
(Continued)

(58) Field of Classification Search
CPC ... B01J 21/02; B01J 27/24; B01J 23/02; B01J 23/10; B01J 23/14; B01J 35/0006;
(Continued)

(56) References Cited

U.S. PATENT DOCUMENTS

| 3,117,169 A | 1/1964 | Coley et al. |
| 4,349,517 A * | 9/1982 | Lysanov ............. C04B 35/5831 423/290 |

(Continued)

FOREIGN PATENT DOCUMENTS

| CN | 10 6694017 | * 5/2017 |
| CN | 106694017 A | 5/2017 |

(Continued)

OTHER PUBLICATIONS

Paramita Banerjee et al., "First principles design of Li functionalized hydrogenated h-BN nanosheet for hydrogen storage." International Journal of Hydrogen Energy 41, pp. 14437-14446. (Year: 2016).*

(Continued)

*Primary Examiner* — Patricia L. Hailey
(74) *Attorney, Agent, or Firm* — BakerHostetler

(57) ABSTRACT

Disclosed is a catalyst comprising: a composition having a formula $BN_xM_yO_z$ wherein B represents boron, N represents nitrogen, M comprises a metal or metalloid, and O represents oxygen, x ranges from 0 to 1, y ranges from 0.01 to 5.5; and z ranges from 0 to 16.5. The catalyst may be suitable for converting alkanes to olefins.

20 Claims, 7 Drawing Sheets

(51) Int. Cl.
  *B01J 23/14* (2006.01)
  *B01J 23/10* (2006.01)
  *B01J 23/02* (2006.01)
  *B01J 35/00* (2006.01)
  *B01J 37/04* (2006.01)
  *C07C 5/48* (2006.01)
  *B01J 37/08* (2006.01)

(52) U.S. Cl.
  CPC ............ *B01J 35/0006* (2013.01); *B01J 37/04* (2013.01); *B01J 37/08* (2013.01); *C07C 5/48* (2013.01); *C07C 2521/08* (2013.01); *C07C 2523/02* (2013.01); *C07C 2523/10* (2013.01); *C07C 2523/14* (2013.01); *C07C 2527/24* (2013.01)

(58) Field of Classification Search
  CPC ...... B01J 37/04; B01J 37/08; B01J 2523/305; C07C 5/48; C07C 2521/08; C07C 2523/02; C07C 2523/10; C07C 2523/14; C07C 2527/24; C22C 2026/003; B22F 2302/205
  USPC ........ 502/200, 202, 300; 423/276, 277, 279; 585/654
  See application file for complete search history.

(56) References Cited

U.S. PATENT DOCUMENTS

| | | | | |
|---|---|---|---|---|
| 7,723,258 | B2 * | 5/2010 | Rei | ............ B01J 23/40 423/213.5 |
| 9,059,361 | B1 * | 6/2015 | Legg | ............ H01L 39/125 |
| 10,501,322 | B2 * | 12/2019 | Hermans | ............ C01B 21/0648 |
| 2017/0066700 | A1 * | 3/2017 | Hermans | ............ B01J 27/22 |
| 2017/0313635 | A1 | 11/2017 | Hermans et al. | |
| 2019/0119166 | A1 * | 4/2019 | Hakeem | ............ C22C 29/12 |
| 2019/0329228 | A1 * | 10/2019 | Kim | ............ B01J 37/0221 |

FOREIGN PATENT DOCUMENTS

| | | | | |
|---|---|---|---|---|
| FR | 2 986 153 | * | 8/2013 | ............ A61K 8/19 |
| WO | WO-2013114029 A1 | * | 8/2013 | ............ B01J 13/22 |
| WO | WO 2017/044711 | | 3/2017 | |

OTHER PUBLICATIONS

Ning Zhang et al., "The influence of metal Mg on micromorphology and crystallinity of spherical hexagonal boron nitride." Materials Research Bulletin 68, pp. 179-184. (Year: 2015).*

Jason A. Loiland et al., "Boron-Containing Catalysts for the Oxidative Dehydrogenation of Ethane/Propane Mixtures." Industrial and Engineering Research, 58, pp. 2170-2180. (Year: 2019).*

Shi et al.; "Edge-hydroxylated Boron Nitride for Oxidative Dehydrogenation of Propane to Propylene"; ChemCatChem; vol. 9 Issue 10; May 2017; p. 1788-1793.

Venegas et al.; "Selective Oxidation of n-Butane and Isobutane Catalyzed by Boron Nitride"; ChemCatChem; vol. 9 Issue 12; Jun. 2017; p. 2118-2127.

Shi et al.; "Selective oxidative dehydrogenation of ethane to ethylene over a hydroxylated boron nitride catalyst"; Chinese Journal of Catalysis.; vol. 38; 2017; p. 389-395.

Grant et al.; "Selective oxidative dehydrogenation of propane to propene using boron nitride catalysts"; Science; vol. 354 Issue 6319; Dec. 2016; 7 pages.

International Patent Application No. PCT/IB2019/056382; Int'l Search Report and the Written Opinion; dated Feb. 10, 2020; 21 pages.

* cited by examiner

FUNCTIONALIZED BORON NITRIDE CATALYSTS FOR THE PRODUCTION OF LIGHT OLEFINS FROM ALKANE FEEDS VIA OXIDATIVE DEHYDROGENATION

TECHNICAL FIELD

The disclosure generally relates to the process for the conversion of alkanes to light olefins, and more specifically for boron-based catalysis for the conversion of alkanes to light olefins via oxidative dehydrogenation.

BACKGROUND

Light olefins are often produced commercially through steam or catalytic cracking of petroleum-derived hydrocarbons, through direct catalytic dehydrogenation of alkanes, or through a coal-based methanol-to-olefins process. The oxidative dehydrogenation (ODH) of alkanes may be a desirable alternative to foregoing the technologies. Oxidative dehydrogenation requires a highly selective catalyst to avoid over-oxidation of the alkane and generated alkene to deep oxidation products (carbon monoxide CO and carbon dioxide $CO_2$), which are thermodynamically favored at reaction temperatures (typically 400° C. to 700° C.). Conventional ODH catalysts studied in the literature are typically vanadium V-, molybdenum Mo-, nickel Ni-, magnesium Mg-, cobalt Co-, and manganese Mn-based materials for propane ODH and may exhibit alkane conversions in the range of 10-30% with olefin selectivities in the range of 30-60%, and the major byproducts being CO and $CO_2$.

U.S. Published Patent Application 2017/0066700 A1 describes methods of oxidative dehydrogenation of an alkane to a corresponding olefin using boron or nitride containing catalysts.

Chinese Patent Application 106694017 describes a catalyst for producing olefins from alkanes via oxidative dehydrogenation. The catalyst is a sold metal catalyst composed of nitrogen and boron where boron is $sp^2$ or $sp^3$ hybridized of hexagonal boron nitride, cubic boron nitride, rhombohedral boron nitride, boron nitride crystal structure, $sp^2$ or $sp^3$ hybrid hexagonal boron nitride.

U.S. Published Patent Application 2017/03136535 describes heterogeneous catalysts comprising boron nitride for the oxidative dehydrogenation of alkanes or oxidative coupling of alkanes. The boron nitride catalysts have increased surface area and may be in the form of boron nitride nanotubes and boron nitride nanomeshes.

International Published Patent Application WO 2017/0704411 describes catalysts containing boron, nitride, or both for catalysis of the oxidative coupling of methane.

There remains a need in the art for improved ODH catalysts.

SUMMARY

Aspects of the present disclosure relate to boron-based catalysts for oxidative dehydrogenation of alkanes. In various aspects, a catalyst may comprise a composition having a formula $BN_xM_yO_z$. According to the formula, B may represent boron, N may represent nitrogen, M may comprise a metal or metalloid, and O may represent oxygen. Values for x may be from 0 to 1; for y, from 0.01 to 5.5; and, for z, from 0 to 16.5. In further aspects, x may be from 0.01 to 1 or from 0.9 to 1. Values for y and z may range from 0.01 to 0.06. In some aspects, y and z may be equal or y and z may both be 0.06. In certain aspects, x may be equal to 1 and boron may be present as a component of boron nitride.

In further aspects of the present disclosure, M and O may be speciated as magnesium oxide. In alternative aspects, M is strontium and M and O are speciated as strontium oxide.

The disclosed catalyst may comprise boron nitride which may be a hexagonal boron nitride. In some aspects, the boron nitride may be cubic, wurtzitic, or amorphous boron nitride. The disclosed catalyst may comprise a support. In various aspects, the disclosed catalyst is suitable for converting an alkane to an olefin that may comprise a $C_2$ or higher alkene. The olefin may comprise ethylene, propylene, butylene, isobutene, or a combination thereof.

The present disclosure further relates to a method of forming a catalyst. The method may comprise combining one or more of elemental boron and boron nitride with one or more of (i) a metal, (ii) a metalloid, (iii) an oxide of a metal, and (iv) an oxide of a metalloid to form a mixture; and milling the mixture. The milled mixture may be calcined at a temperature of about 100° C. to about 800° C. for at least a first time period to provide the catalyst. In some aspects, the calcining proceeds at a temperature of about 100° C. to about 800° C. The calcining may comprise heating at about 120° C. for a first time period. In certain aspects, the calcining may occur for at least a second time period. The milling may comprise grinding the mixture to a particle size of less than 0.5 mm.

In yet further aspects, the present disclosure relates to a method of converting alkanes to olefins. The method may comprise contacting a hydrocarbon source with a catalyst and an oxidant at a temperature of from about 400° C. to about 700° C. The catalyst may comprise a composition having a formula $BN_xM_yO_z$. According to the formula, B may represent boron, N may represent nitrogen, M may comprise a metal or metalloid, and O may represent oxygen, x ranges from 0 to 1, y ranges from 0.01 to 5.5; and z ranges from 0 to 16.5.

BRIEF DESCRIPTION OF THE DRAWINGS

The above-mentioned and other features and advantages of this disclosure, and the manner of attaining them, will become apparent and be better understood by reference to the following description of one aspect of the disclosure in conjunction with the accompanying drawings, wherein.

DETAILED DESCRIPTION

Figure 1:
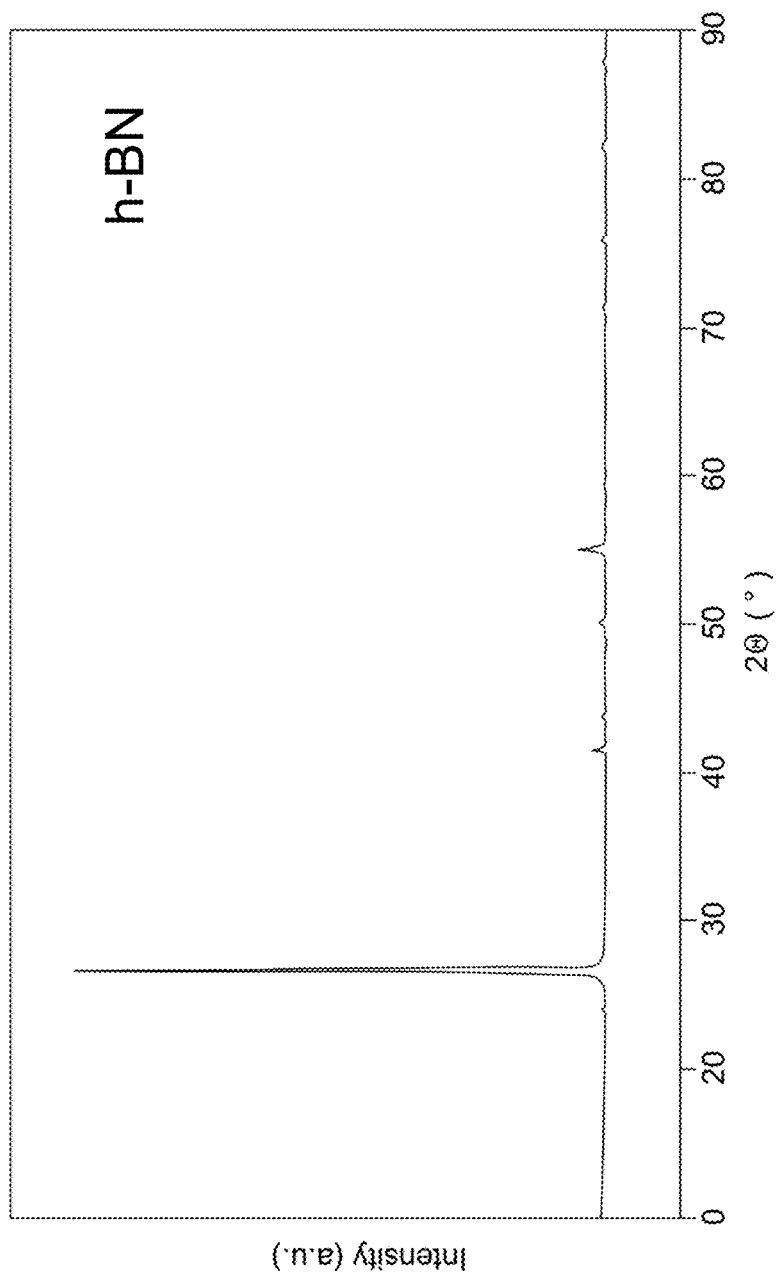
FIG. 1 shows the powder XRD pattern of a hexagonal-boron nitride sample.

The present disclosure can be understood more readily by reference to the following detailed description of the disclosure and the Examples included therein. It is also to be understood that the terminology used herein is for describing particular aspects only and is not intended to be limiting.

Various combinations of elements of this disclosure are encompassed by this disclosure, e.g., combinations of elements from dependent claims that depend upon the same independent claim.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including matters of logic with respect to arrangement of steps or operational flow; plain meaning derived from grammatical organization or punctuation; and the number or type of aspects described in the specification.

Light olefins are produced commercially through steam or catalytic cracking of petroleum-derived hydrocarbons, direct catalytic dehydrogenation of alkanes, and the coal-based methanol-to-olefins process. These processes may suffer from various disadvantages including capital-intensive unit operations, emissions of large volumes of carbon dioxide into the atmosphere, consumption of large amounts of energy, severe catalyst coking resulting in the need for frequent catalyst regeneration, and thermodynamic limitations. The oxidative dehydrogenation (ODH) of alkanes is a desirable alternative to the existing technologies because catalyst coking may be avoided and the ODH reaction is free of any equilibrium constraints. However, the oxidative reaction requires a highly selective catalyst to avoid over-oxidation of the alkane and produced alkene to deep oxidation products (CO, $CO_2$); CO and $CO_2$ are thermodynamically favored at reaction temperatures.

Existing commercial production facilities may avoid the ODH process because of the large quantities of CO and $CO_2$ that are formed via undesired side reactions over conventional catalysts. For example, most catalysts studied in the literature (V-, Mo-, Ni-, Mg-, Co-, and Mn-based materials) for ODH of propane exhibit alkane conversions in the range of 10-30% with olefin selectivities in the range of 30-60%, with the major byproducts being CO and $CO_2$. Additionally, most conventional catalysts from the literature cannot maintain their level of performance for extended periods of time, as the active sites responsible for the selective formation of olefins tend to sinter or agglomerate in the presence of oxygen. The present disclosure provides boron-based materials to catalyze the oxidative dehydrogenation of an alkane mixture to form alkenes. The boron-based materials may be contacted simultaneously with an alkane mixture and an oxidant ($O_2$, air, $CO_2$, halogen, $N_2O$, elemental sulfur) in the absence or presence of steam at temperatures in the range of 450-700° C. to selectively form alkenes. The disclosed boron-based materials exhibit very high thermal stability in the presence of oxygen and may thus selectively catalyze the ODH reaction for extended periods of time.

The present disclosure describes methods and materials that can selectively oxidize alkanes to olefins at reasonable conversions. Described herein are boron-based materials as catalysts for the oxidative dehydrogenation of alkanes to form alkenes. These materials may be contacted simultaneously with an alkane and an oxidant ($O_2$, air, $CO_2$, as well as halogen, $N_2O$, elemental sulfur as diluents) in the absence or presence of steam at temperatures in the range of 450-700° C. to selectively form alkenes. The materials disclosed in this document exhibit very high thermal stability in the presence of oxygen, and thus may selectively catalyze the reaction for extended periods.

A method of converting alkanes to olefins may comprise contacting a hydrocarbon-containing feed with a catalyst and an oxidant at a temperature of from about 400° C. to about 700° C. The catalyst may comprise a promoted boron-nitride. Under the prescribed reaction conditions, the hydrocarbon-containing feed may be oxidatively dehydrogenated to form an olefin.

Provided herein are catalysts for oxidative dehydrogenation of lower alkanes. The disclosed catalysts comprise functionalized boron nitride. As used herein, "functionalized boron" or "functionalized boron nitride" may refer to boron or boron nitride combined with one or more functional components, or "promoters," such as one or more additional disclosed compounds or materials. To provide the functionalized boron nitride, boron nitride may be combined with one or more of a metal, a metalloid, an oxide of a metal or metalloid, metal or metal oxide nanoparticles. The term "functionalized" when used with respect to boron or boron nitride means the same as, and is used interchangeably with, "promoted" boron or boron nitride. The functional components are also known as promoters.

Suitable metals may include, but are not limited to, noble metals, such as platinum and palladium particles, copper, gallium, lithium, sodium, cesium, magnesium, calcium, strontium, manganese, tin, zinc, lanthanum, aluminum, barium, yttrium, titanium, zirconium, cerium, germanium, niobium, vanadium, chromium, molybdenum, rhenium, and tungsten. Metalloids may include but are not limited to, silicon, antimony, or tellurium. Oxides of metals/metalloids may include but are not limited to copper oxide, gallium (I) oxide, gallium (III) oxide, lithium oxide, sodium oxide, cesium oxide, magnesium oxide, calcium oxide, strontium oxide, zinc oxide, lanthanum oxide, aluminum oxide, tin oxide, antimony (III) oxide, antimony pentoxide, barium oxide, yttrium oxide, ytterbium oxide, silicone dioxide, titanium dioxide, zirconium dioxide, cerium (IV) oxide, germanium dioxide, niobium pentoxide, vanadium pentoxide, chromium trioxide, molybdenum trioxide, rhenium trioxide, tungsten trioxide, magnesium oxide, and strontium oxide.

Functionalized boron nitride catalysts for oxidative dehydrogenation of lower alkanes may comprise a metal, metalloid, or oxide of a metal or metalloid. The catalysts may be characterized by having a composition expressed by a general formula (I) below:

$$BN_xM_yO_z \qquad (I)$$

wherein B is boron, N is nitrogen, M is a metal or metalloid, and O is oxygen, x is the molar ratio of nitrogen to boron and ranges from 0 to 1, y is the molar ratio of M to boron and ranges from 0.01 to 5.5, and z is the molar ratio of oxygen to boron and ranges from 0 to 16.5. In certain examples, M may comprise noble metals, alkaline earth metals, lanthanoids, or transition metals. In further aspects, the catalyst may be promoted by a metal oxide. Boron may be present as a component as (i) boron nitride, (ii) free boron, or as (iii) both boron nitride and free boron, and M and O are speciated with one or more of a metal, a metalloid, an oxide of a metal, or an oxide of a metalloid. That is, boron may be present as a component of boron nitride, free boron, or a combination thereof. Where boron is present only as free boron, x is 0. Although there is no subscript shown for B in general formula (I), it should be understood to be 1.

M may comprise a metal selected from noble metals, alkaline earth metals, lanthanoids, or transition metals. M may comprise platinum, silver, lanthanum, cerium, zirconium, titanium, tin, strontium, magnesium, tungsten, copper, gallium, lithium, sodium, calcium, manganese, zinc, aluminum, lead, barium, gallium, yttrium, ytterbium, silicon, cesium, germanium, niobium, vanadium, chromium, molybdenum, rhenium, or a combination thereof. In an example, M may be magnesium and the catalyst may be magnesium oxide functionalized boron nitride. In a yet further example, M may be strontium and the catalyst may be strontium oxide functionalized boron nitride.

Table 1 summarizes the metal oxides that may form the functionalized particles that may be combined with the boron nitride. Also shown are the metal oxidation states and oxygen to metal ratios of the metal oxides.

TABLE 1

Oxides of metals and metalloids.

| Compound | M Oxidation state | O/M |
| --- | --- | --- |
| $Cu_2O, Ga_2O, Li_2O, Na_2O, Cs_2O$ | +1 | 0.5 |
| $MgO, CaO, SrO, MnO, SnO, ZnO$ | +2 | 1 |
| $La_2O_3, Al_2O_3, Sb_2O_3, Ba_2O_3, Ga_2O_3, Y_2O_3, Yt_2O_3$ | +3 | 1.5 |
| $SiO_2, TiO_2, ZrO_2, CeO_2, GeO_2$ | +4 | 2 |
| $Sb_2O_5, Nb_2O_5, V_2O_5$ | +5 | 2.5 |
| $CrO_3, MoO_3, ReO_3, WO_3,$ | +6 | 3 |

The one or more additional compounds combined with boron nitride to provide the functionalized boron nitride catalyst may be present in any useful amount. For example, the functional component or promoter may be present in an amount up to 95 wt. % based on the total weight of the catalyst. In further examples, the promoter may be present from about 1 wt. % to about 95 wt. % based on the total weight of the catalyst. In yet further examples, the promoter is present from about 1 wt. % to about 20 wt. %, or from about 1 wt. % to about 10 wt. %, based on the total weight of the catalyst.

The functionalized-boron nitride catalyst may be used in any appropriate form. For example, the catalyst may be pelletized or powdered. The pelletized catalyst may be used the form of a fixed catalyst bed, or a powdered catalyst, for example in the form of a fluidized catalyst bed. The functionalized boron nitride catalyst may be in any appropriate structural form. For example, amorphous boron nitride (amorphous BN) particles, wurtzitic boron nitride (w-BN) particles, and hexagonal boron nitride (h-BN) particles are suitable types of BN.

The present disclosure provides a process for producing olefins that comprises oxidative dehydrogenation of a hydrocarbon-containing feed, characterized by the use of the above-described catalyst. The hydrocarbon-containing feed introduced to a reactor system for ODH may comprise alkanes. Suitable alkanes for ODH may comprise ethane, propane, n-butane, isobutane, n-pentane and isopentane. The disclosed catalysts are used in oxidative dehydrogenation reactions of such lower alkanes to produce corresponding (or non-corresponding) olefins, more specifically, ethylene from ethane, propylene from propane, n-butene from n-butane, isobutene from isobutane, n-pentene from n-pentane and isopentene from isopentane. In various examples, the oxidation of alkanes in the dehydrogenation process of the present disclosure, features an alkane having 2-6 carbon atoms, straight-chain alkanes, such as an alkane selected from ethane, propane, butane, pentane and hexane. In some examples, the alkane contains 2-4 carbon atoms, selected from ethane, propane and butane. The oxidative dehydrogenation boron-based catalysts employed herein may be particularly useful for the production of ethylene and propylene from ethane and propane, respectively. It is noted however, that the disclosed catalysts may be used to form both corresponding and non-corresponding lower olefins from higher alkanes; such as ethylene from ethane as well as from propane and butane; and such as propylene from propane as well as butane.

Moreover, the oxidative dehydrogenation boron-based catalysts employed herein may be particularly useful for mixed alkane feeds. The hydrocarbon-containing feed may comprise a single alkane or may be a mixture of more than one. Two or more gas streams can be fed to the reactor system, the gas stream to form a mixed stream within the reactor. For example, one stream comprising oxygen and the other gas stream comprising an alkane or mixture of alkanes, such as ethane, can be fed to the reactor separately. The one or more gas stream may further comprise an inert gas stream or diluent, described further herein. In one example, the hydrocarbon-containing feed may comprise 70% hydrocarbon (HC, with a molar composition of 25% ethane, 75% propane), 27% $O_2$+3% $N_2$.

The hydrocarbon feed may further comprise a diluent gas. The use of inert diluents in catalytic vapor phase processes is known. Diluents may improve catalyst selectivity and may minimize contributes from gas-phase reactions. Thus, it has been frequently proposed to employ hydrogen, nitrogen, carbon dioxide and steam as inert diluents. In most cases, however, inert diluents are not used. Nitrogen and carbon dioxide rarely exert any beneficial effect as diluents. Steam may be beneficial as an inert diluent in certain dehydrogenation reactions. For instance, in the ODH of butene to butadiene using conventional Zn-ferrite catalysts, steam is included in the feed, and is necessary for the catalyst to demonstrate high activity. However, a steam diluent is not essential for the instant disclosure. Steam may be used for suppressing heat. Hydrogen is sometimes used as an inert diluent in catalytic dehydrogenation processes, and its use is especially advantageous when dehydrogenating higher easily cracked hydrocarbons. However, $H_2$ may not be a preferable diluent in the present disclosure where the oxidant comprises oxygen. Co-feeding $H_2$ and $O_2$ may present a flammability hazard. Additionally, further $H_2$ may be more reactive than the hydrocarbons, and may thus consume the $O_2$ before the hydrocarbons have a chance to react. This would limit the HC conversion. In various aspects, the diluent gas is free of or substantially free of hydrogen. Suitable diluent gases may comprise nitrogen, argon, neon, helium, krypton, xenon, carbon monoxide, carbon dioxide, steam, or a combination thereof. In some examples, the ODH reaction occurs in the absence of steam. Steam may be co-fed with the hydrocarbon feed as a means of generating hydroxide —OH groups at the boron-nitride catalyst surface, which may be active in catalyzing the reaction.

As provided above, the hydrocarbon feed may be contacted with the catalyst in the presence of an oxidant at a temperature of from about 400° C. to about 700° C. In certain examples, the oxidant may comprise molecular oxygen. Pure oxygen or air may be used at a ratio of 0.2 to 20 moles of alkane per mole of oxygen. The oxidant may comprise oxygen, air, nitrous oxide $N_2O$, carbon dioxide, or a combination thereof. Certain conventional boron catalysts, such as boron carbide, have been described as catalysts for oxidative dehydrogenation of light alkanes to olefins, as in Shi et al. Chem. Cat. Chem. 9 (2017) 1788-1793, for example. However, these carbide catalysts typically proceed in the presence of molecular oxygen as the oxidant. The boron-based catalysts of the present disclosure facilitate ODH of alkanes using alternative oxidants (and/or diluents) such as $CO_2$, $N_2O$, and halogens.

Although some catalyst is necessary, the amount of the catalyst in the disclosed process is not a critical variable. Preferably, a catalytically effective amount of the catalyst is used, that is to say an amount sufficient to promote the alkane oxidative dehydrogenation and/or alkene oxidation reaction. Although a specific quantity of catalyst is not critical to the disclosure, preference may be expressed for use of the catalyst in such an amount that the weight hourly space velocity (WHSV, defined as kilograms $(kg)_{hydrocarbon}$ $kg_{cat}^{-1}$ hour $(h)^{-1}$) is from 1 to 5000 $h^{-1}$, or of from 1 to 200 $h^{-1}$, or of from 1 to 100 $h^{-1}$, or of from 1 to 50 $h^{-1}$.

The oxidative dehydrogenation catalysts of general formula (I) of the present disclosure may be unsupported or may be supported on a refractory inorganic carrier. The catalyst support may be used to improve catalytic activity level and physical durability. As the refractory inorganic carrier, those generally used in preparation of this type of catalyst may be used, the representative examples thereof including silica, alumina, titanic, zirconia, ceria, ceria-zirconia, silica-alumina, silica-titania and silica-zirconia. In particular, silica and silica-alumina may be particularly useful because they give higher yield of object products. The ratio of silica in the silica-alumina catalyst system normally ranges from 10% by weight to less than 100% by weight. The amount of the catalytically active component to be carried is normally between 10% and 90% by weight of the refractory inorganic carrier. As an example, the disclosed methods may proceed using a functionalized boron nitride catalyst on a silicon carbide support.

The reaction conditions for carrying out the oxidative dehydrogenation are subject to no critical limitation. The present alkane oxidative dehydrogenation process may comprise directing a feedstream comprising an alkane containing 2 to 6 carbon atoms to a reactor. The stream may be contacted with an oxidant thereby resulting in oxidative dehydrogenation of the alkane and/or oxidation of the alkene. The oxidant may comprise oxygen or an oxygen alternative as described herein. Ranges for the molar ratio of alkane to oxidant, such as oxygen, is from about 0.5:1 to about 20:1. In the alkane oxidative dehydrogenation process, typical reaction pressures are 0.1-20 bar, and typical reaction temperatures are 200-800° C., specifically 400° C. to 700° C. In general, the product stream may comprise water in addition to the desired olefin product. Water may easily be separated from said product stream, for example by cooling down the product stream from the reaction temperature to a lower temperature, for example room temperature, so that the water condenses and can then be separated from the product stream.

The hydrocarbon-containing feed as described herein may be contacted with an oxidative dehydrogenation functional boron nitride catalyst under such conditions as: at a weight hourly space velocity of 1 to 500 $h^{-1}$, or more specifically at 1 $h^{-1}$ to 100 $h^{-1}$; at a temperature between 250° C. and 800° C., or more specifically from about 400° C. to about 700° C.

The ODH reaction may be performed under ambient or atmospheric pressure. Ambient pressure may be described as that denoted in STP (standard temperature and pressure), which is one atmosphere (atm, 1.01325 bar). In further conditions, the ODH reaction may be performed under reduced or elevated pressure. Elevated pressure may be considered pressure up to 10 bar. In the alkane oxidative dehydrogenation process according to the present disclosure, the pressure may be maintained at 0.1 to 20 bar pressure (i.e., "bar absolute pressure value"). Further, in one aspect, a pressure of 0.1 to 15 bar, or 5 to 10 bar, or 1 to 5 bar may be maintained.

The reactor system for effecting the ODH process may not be critical. Suitable reactor systems may comprise a fixed bed system, moving bed system or fluidized bed system. The reactor system may be a one-pass system or recycling system.

Olefins formed according to the disclosed process may comprise an alkane dehydrogenation counterpart, i.e., a corresponding olefin. For example, in the case of ethane, such products may comprise ethylene and in the case of propane, such products may comprise propylene, and the like. However, in the same process, the dehydrogenation product may be further oxidized to the corresponding carboxylic acid under the same conditions; the carboxylic acid may or may not contain one or more unsaturated carbon-carbon double bond. As described above, an alkane having 2-6 carbon atoms such as ethane or propane may be contacted with the functionalized boron nitride catalyst and oxidant. For ethane, the product of the alkane oxidative dehydrogenation process may comprise ethylene and/or acetic acid, preferably ethylene. Further, with propane, the product of alkane oxidative dehydrogenation process may comprise propylene and/or acrylic acid, preferably acrylic acid. It is noted however, that the disclosed catalysts may be used to form both corresponding and non-corresponding lower olefins from higher alkanes; such as ethylene from ethane as well as from propane and butane; such as propylene from propane as well as butane.

Methods

In this section, description of the making of catalyst described herein are presented. Though the following is illustrated using example values, processes, and materials, it is contemplated that other materials, processes, and values may be used according to design specifications.

Formation of the oxidative dehydrogenation catalysts described herein is not subject to any critical limitations, but any of conventionally practiced methods or known methods for preparation of this type of catalysts can be used. One example of a method for catalyst is now described. The functionalized boron nitride catalyst may be produced by combining boron nitride powder and the functional component. For example, the boron nitride may be physically mixed with one or more metal (or metalloid) oxide powders. The resulting mixture may be milled and subsequently calcined to provide the functionalized boron nitride catalyst. The calcination process may be as known in the art and may comprise heating from 100° C. to 800° C. over successive periods of heating and maintaining. The calcined catalyst may be pressed and screened to a specific particle size.

Also presented herein are methods of forming alkenes from alkanes using the disclosed boron-based catalysts. The method may comprise contacting a hydrocarbon source with a catalyst and an oxidant at a temperature of from about 400° C. to about 700° C. The catalyst may comprise a functionalized boron nitride. The functionalized boron nitride may comprise boron nitride and one or more of a metal/metalloid oxide, a metal, or a metalloid.

Properties

The catalyst may be used in a process of oxidative dehydrogenation of alkanes to produce light olefins. Such developments may produce higher productivity, longer catalyst life, adaptability to certain feedstreams and/or cost reduction in raw material, equipment and process operation. One example of a feedstream to which the disclosed catalyst would be adaptable may be a feedstream that is predominantly alkanes. However, the catalyst may be useful in converting a mixed alkane feedstream.

Methods of the present disclosure employ functionalized boron nitride catalysts for in a process of oxidative dehydrogenation of alkanes to produce light olefins. These developments may produce higher productivity, longer catalyst life, adaptability to certain feedstreams and/or cost reduction in raw material, equipment and process operation. With these boron-based catalysts, the ODH process may proceed in the presence of oxygen or of an alternative oxidant (such as nitrous oxide, elemental sulfur, halogens, and/or carbon dioxide.

The ODH methods described herein using a functionalized boron nitride catalyst may provide certain conversion rates for the hydrocarbon and oxidant (oxygen) of the hydrocarbon feed with which the catalyst is contacted. For example, the functionalized boron nitride catalyst may provide a hydrocarbon conversion rate of at least 30%, or at least 40%, or at least 50%, for a hydrocarbon feed comprising 70% hydrocarbon, 27% oxygen, and 3% nitrogen at total gas flow rate of 175 sccm and WHSV of 41 $h^{-1}$.

Moreover, the disclosed ODH methods using the functionalized boron nitride catalyst may provide a certain selectivity for the olefin. For example, the catalyst may provide an ethylene selectivity of at least 30% for a hydrocarbon feed comprising 70% hydrocarbon, 27% oxygen, and 3% nitrogen at total gas flow rate of 175 sccm and WHSV of 41 $h^{-1}$. In further examples, the catalyst may provide a propylene selectivity of at least 25% for a hydrocarbon feed comprising 70% hydrocarbon, 27% oxygen, and 3% nitrogen at total gas flow rate of 175 standard cubic centimeter per minute (sccm) and WHSV of 41 $h^{-1}$.

The disclosed catalysts may further be useful for a broader range of feeds than conventional alternatives because the disclosed catalysts have demonstrated activity to convert various alkanes in a single hydrocarbon feed.

The disclosure having been generally described, the following examples are given as particular embodiments of the disclosure and to demonstrate the practice and advantages thereof. It is understood that the examples are given by way of illustration and are not intended to limit the specification or the claims to follow in any manner.

Aspects

The present disclosure relates to at least the following aspects.

Aspect 1. A catalyst comprising: a composition having a formula $BN_xM_yO_z$ wherein B represents boron, N represents nitrogen, M comprises a metal or metalloid, and O represents oxygen, x ranges from 0 to 1, y ranges from 0.01 to 5.5; and z ranges from 0 to 16.5.

Aspect 2. The catalyst of aspect 1, wherein x ranges from 0.01 to 1.

Aspect 3. The catalyst of aspect 1, wherein x ranges from 0.9 to 1.

Aspect 4. The catalyst of aspect 1, wherein x ranges from 0.95 to 1.

Aspect 5. The catalyst of aspect 1, wherein x ranges from 0.99 to 1.

Aspect 6. The catalyst of any of aspects 1-5, wherein y and z range from 0.01 to 0.06.

Aspect 7. The catalyst of aspect 6, wherein y and z are 0.06.

Aspect 8. The catalyst of aspect 7, wherein x is equal to 1 and boron is present as a component of boron nitride.

Aspect 9. The catalyst of aspect 6, wherein y and z are equal.

Aspect 10. The catalyst of any of aspects 3-5, wherein M and O is speciated as magnesium oxide.

Aspect 11. The catalyst of any of aspects 3-5, wherein M is strontium and M and O is speciated as strontium oxide.

Aspect 12. The catalyst of any of aspects 1-11, wherein the boron nitride is hexagonal boron nitride.

Aspect 13. The catalyst of any of aspects 1-12, wherein the boron nitride is cubic, wurtzitic, or amorphous boron nitride.

Aspect 14. The catalyst of any of aspects 1-13, further comprising a support.

Aspect 15. The catalyst of any of aspects 1-14, wherein the catalyst is suitable for converting an alkane to an olefin and wherein the olefin comprises ethylene, propylene, butylene, isobutene, or a combination thereof.

Aspect 16. The catalyst of any of aspects 1-14, wherein the catalyst is suitable for converting an alkane to an olefin and wherein the olefin comprises a $C_2$ or higher alkene.

Aspect 17. A method of forming a catalyst, the method comprising: combining one or more of elemental boron and boron nitride with one or more of (i) a metal, (ii) a metalloid, (iii) an oxide of a metal, and (iv) an oxide of a metalloid to form a mixture; and milling the mixture; calcining the milled mixture at a temperature of about 100° C. to about 800° C. for at least a first time period to provide the catalyst.

Aspect 18. The method of aspect 15, wherein calcining proceeds at a temperature of about 100° C. to about 800° C.

Aspect 19. The method of aspect 15, wherein the calcining comprises heating at about 120° C. for a first time period.

Aspect 20. The method of aspect 15, wherein the calcining occurs for at least a second time period.

Aspect 21. The method of aspect 15, wherein the milling comprises grinding the mixture to a particle size of less than 0.5 mm.

Aspect 22. A method of converting alkanes to olefins, the method comprising: contacting a hydrocarbon source with a catalyst and an oxidant at a temperature of from about 400° C. to about 700° C., wherein the catalyst comprises a composition having a formula $BN_xM_yO_z$, wherein B represents boron, N represents nitrogen, M comprises a metal or metalloid, and O represents oxygen, x ranges from 0 to 1, y ranges from 0.01 to 5.5; and z ranges from 0 to 16.5.

Aspect 23. A method of converting alkanes to olefins, the method comprising: contacting a hydrocarbon source with a catalyst and an oxidant at a temperature of from about 400° C. to about 700° C., wherein the catalyst comprises a functionalized boron nitride, the functionalized boron nitride comprises boron nitride and a metal oxide, and the hydrocarbon is oxidatively dehydrogenated to form an olefin.

Aspect 24. The method of aspect 23, wherein the catalyst provides a conversion of hydrocarbon of at least 30% for a hydrocarbon feed comprising 70% hydrocarbon, 27% oxygen, and 3% nitrogen at total gas flow rate of 175 sccm and WHSV of 41 $h^{-1}$.

Aspect 25. The method of any one of aspects 23-24, wherein the hydrocarbon source comprises ethane, propane, butane, isobutane, or a combination thereof.

Aspect 26. The method of any one of aspects 23-25, wherein the olefin comprises a propylene, an ethylene, an n-butene, an isobutene, or a combination thereof.

Aspect 27. The method of any one of aspects 23-26, wherein the catalyst is supported.

Aspect 28. A catalyst comprising: a functionalized boron nitride comprising an mixture of boron nitride and a promoter wherein the promoter comprises a metal, a metalloid, an oxide of a metal or an oxide of a metalloid, metal or metal oxide nanoparticles, or a combination thereof.

Aspect 29. The catalyst of aspect 28, wherein the promoter is present in an amount of about 1 wt. % to about 20 wt. % based on the total weight of the catalyst.

Aspect 30. The catalyst of aspect 28, wherein the promoter is present in an amount of about 1 wt. % to about 10 wt. % based on the total weight of the catalyst.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. Unless indicated otherwise, percentages referring to composition are in terms of wt %.

There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Catalyst samples were prepared by physically mixing the metal oxide powder with the BN powder, then milling the mixture. Subsequently, the samples were calcined in air according to the following calcination procedure: heat from room temperature to 120° C. in 19 minutes, hold for 2 hours; heat from 120° C. to 450° C. in 66 minutes, hold for 2 hours; heat from 450° C. to 750° C. in 1 hour, hold for 4 hours. The metal oxides added to BN included tin oxide SnO, cerium oxide-zirconium oxide $CeO_2$—$ZrO_2$, strontium oxide SrO, lanthanum oxide $La_2O_3$, and magnesium MgO, and were added in ratios of 6 moles of metal to 100 moles of BN. All catalyst samples were pressed and sieved to 20-40 mesh size (420-841 micron (μm)) prior to catalytic tests.

Figure 2:
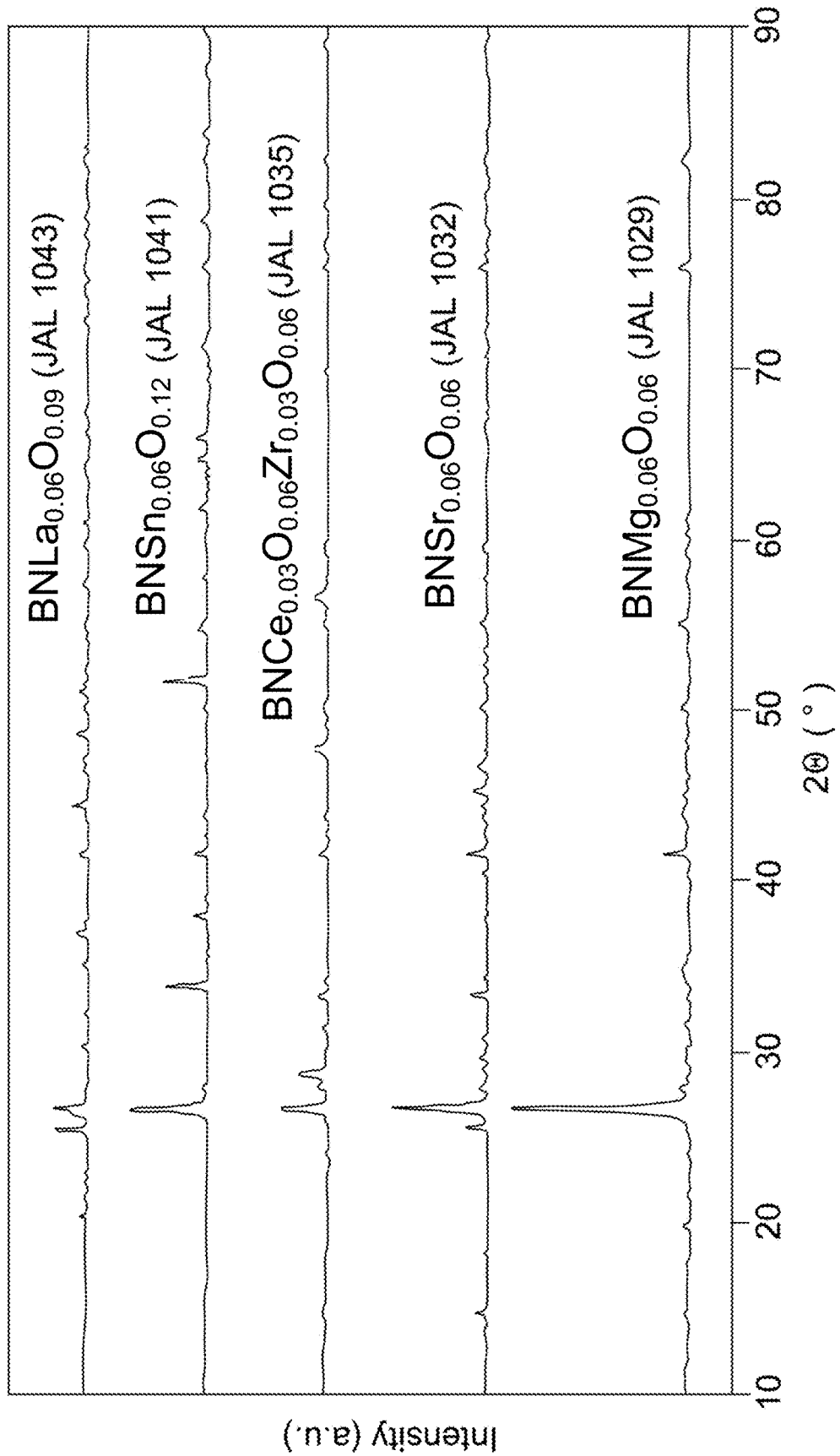
FIG. 2 shows the powder XRD patterns of the metal oxide-promoted BN catalysts.

X-Ray powder diffraction data analysis (XRD) was performed. XRD was conducted on a Philips X'Pert at 15 kilovolts (kV) with a scan of 2 0=10° to 90°. The intensities are relative intensities (arbitrary units, au.). FIG. 1 shows the powder XRD pattern of h-BN (JAL1011). The strong diffraction peak at a 2-theta (2θ) value of 26° represents the (002) plane. The pattern is consistent with the hexagonal crystal structure of boron nitride, and there are no peaks to indicate the presence of crystalline impurities. FIG. 2 shows the powder XRD patterns of the metal oxide-promoted BN catalysts. The XRD pattern for magnesium oxide functionalized boron nitride $BNMg_{0.06}O_{0.06}$ (JAL1029) shows additional peaks at 32°, 35°, and 51° that are associated with magnesium borate ($MgB_2O_5$) and magnesium boron oxide ($Mg(BO_2)_2$) phases. The XRD pattern for strontium oxide functionalized boron nitride $BNSr_{0.06}O_{0.06}$ (JAL1032) shows additional peaks at 16°, 26°, 34°, 42°, 45°, and 47° that are associated with strontium borate. The XRD pattern for cerium oxide/zirconium oxide functionalized boron nitride $BNCe_{0.03}O_{0.06}$—$Zr_{0.03}O_{0.06}$ (JAL1035) shows additional peaks at 27°, 29°, 31°, 33°, 48°, and 58° that are associated with cerium zirconium oxide ($Ce_2Zr_2O_7$) and zirconium oxide ($ZrO_2$). The XRD pattern for tin oxide functionalized boron nitride $BNSr_{0.06}O_{0.06}$ (JAL1041) shows additional peaks at 34°, 38°, 52°, 65°, and 67° that are associated with tin oxide. The XRD pattern for lanthanum oxide functionalized boron nitride $BNLa_{0.06}O_{0.09}$ ($La_2O_3$—BN) (JAL1043) shows additional peaks at 25°, 31°, 35°, 37°, 41°, 45°, 49°, and 52° that are associated with lanthanum borate ($LaBO_3$).

An assessment of catalyst performance for an oxidative dehydrogenation of alkanes was performed. ODH testing was carried out using continuous flow, fixed bed quartz tube reactors (internal diameter, ID=10.5 millimeter (mm,) length=24 inches (in.), 60.96 cm) available from Technical Glass Products, Inc. Gas transfer lines were heated to 250° C. before and after the reactor unit. Heat was supplied to the reactor by a two-zone furnace with a 30.48 cm (12 in.) heating length manufactured by Applied Test Systems (ATS). The temperature was monitored by a 7-point thermocouple (Omega) sheathed in Inconel and placed inside a stainless steel thermal-well secured to the outside wall of the reactor tube. The set points of zone 1 and zone 2 of the furnace were adjusted to provide a 5.08 cm (2 inch) constant temperature region for the catalyst bed.

A 300 milligrams (mg) portion of catalyst (20-40 mesh size, between 420-841 μm) was mixed with about 3 grams of quartz chips (20-40 mesh size) to fill the volume of the 3.81 cm (1.5 in.) long catalyst bed. Catalyst samples were loaded and tested without undergoing any pretreatment. A 70 milligram (mg) portion of quartz wool was placed on each end of the catalyst bed to hold it in place. Tests were conducted at atmospheric pressure and temperatures ranging from 540-560° C. The gas mixture used was 70% hydrocarbon (HC, with a molar composition of 25% ethane, 75% propane)+27% $O_2$+3% $N_2$. Thus, the HC/O2 ratio was typically maintained at 2.6. Nitrogen $N_2$ was fed in the gas mixture as the internal standard to measure the gas expansion factor ($moles_{N2out}/moles_{N2in}$). The total gas flow rate was 175 standard cubic centimeter per minute, sccm (WHSV=41 $kg_{HC}/kg_{cat}/h$). The effluent composition (product mixture) was monitored by online gas chromatography (GC) (Agilent 7890A). The GC was equipped with a flame ionization detector (FID) or with a CP-SilicaPlot capillary column, and a thermal conductivity detector (TCD) with a MS 5 A packed column.

Figure 3A:
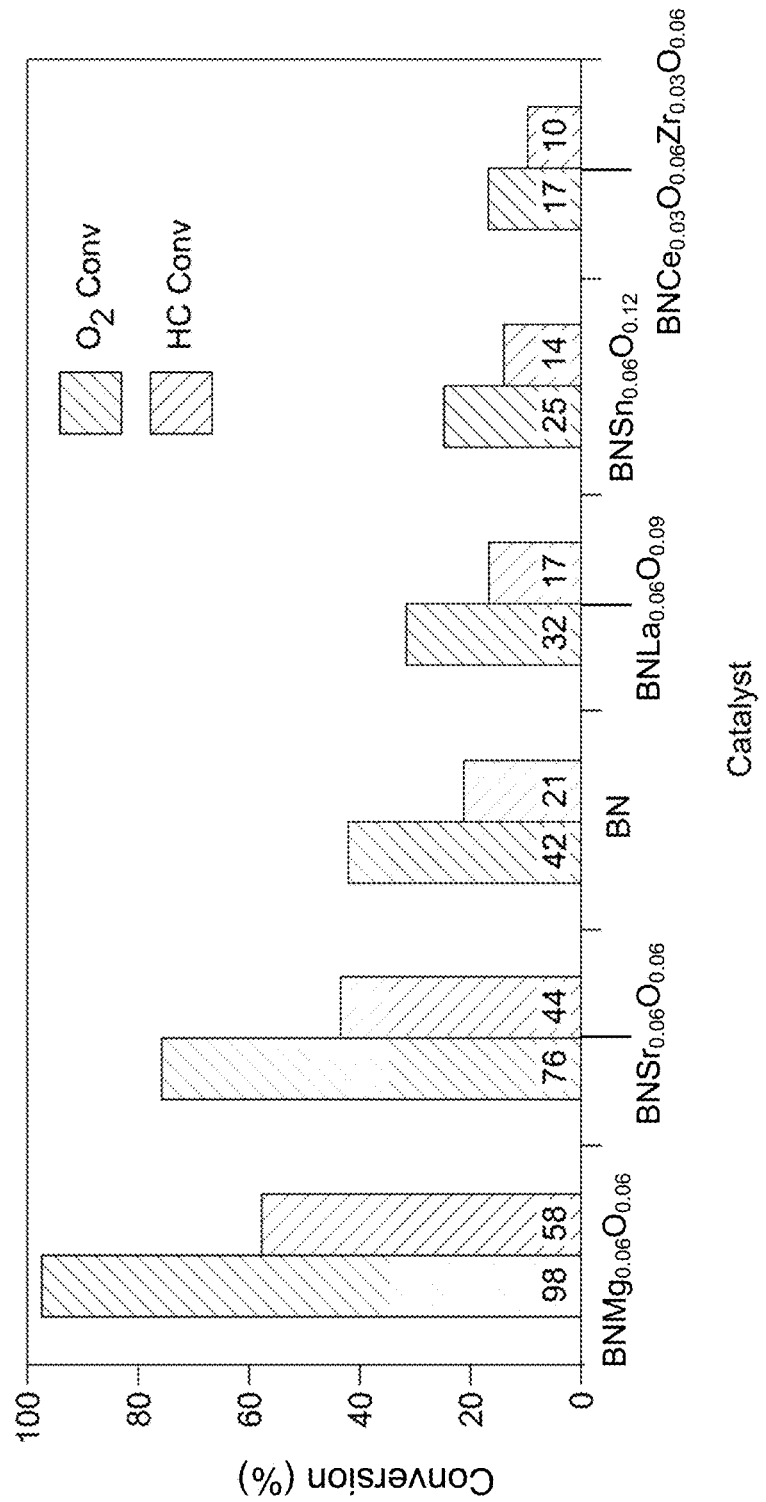
FIGS. 3A and 3B show the (A) conversions (HC, 02) and (B) $C_2$-$C_3$ olefin selectivities for metal-oxide promoted BN samples at 550° C. Reaction conditions: gas composition=70% HC+27% $O_2$+3% $N_2$, Ethane/Propane (E/P) mol ratio=25/75, total gas flow rate=175 standard cubic centimeters per minute (sccm), WHSV=41 $h^{-1}$.
Figure 3B:
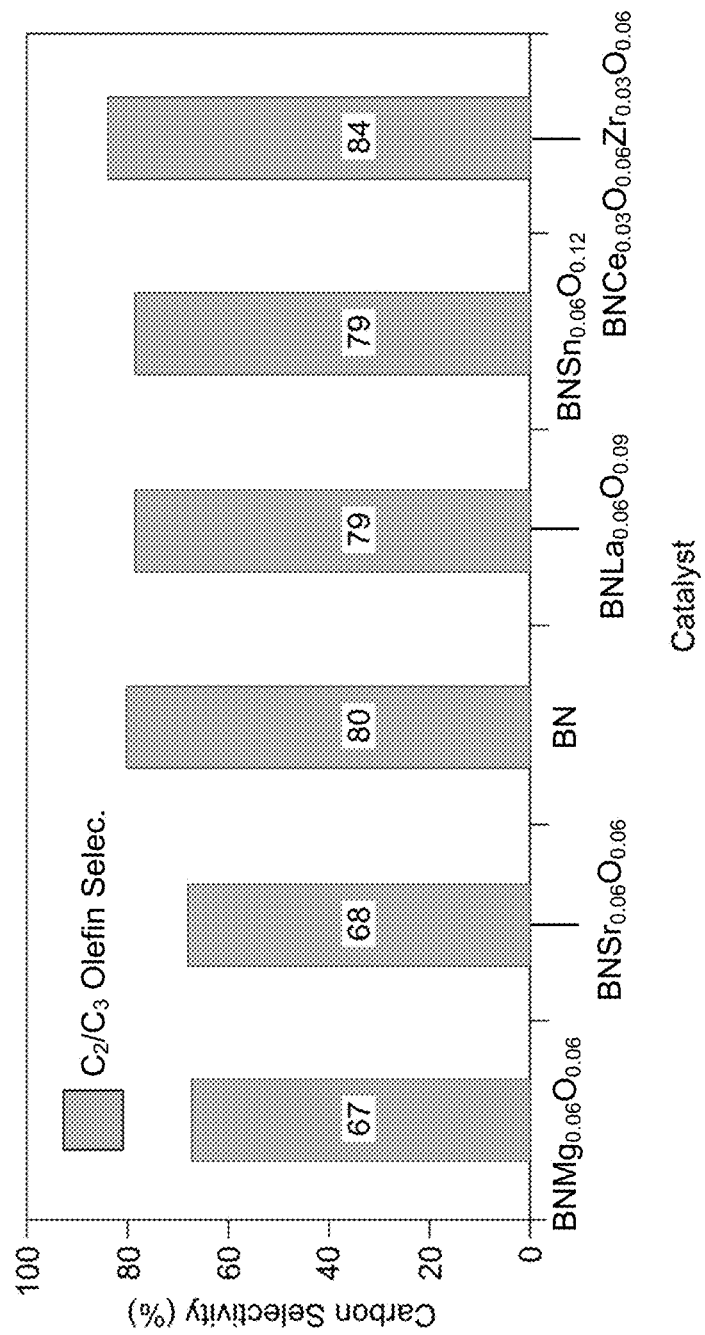

FIG. 3A shows the conversion rates of the oxygen and the hydrocarbon. FIG. 3B shows the carbon selectivity for the different catalysts. The data in FIG. 3A indicate that MgO and SrO promoters enhance the catalytic activity of the boron nitride (BN) catalyst (higher conversion rates), while La, $SnO_2$ and $CeO_2/ZrO_2$ promoters led to lower activity (less conversion). Table 1 presents the conversion and product selectivities for metal-oxide promoted BN samples at 550° C. shown in FIGS. 3A and 3B. Reaction conditions:

gas composition=70% HC+27% $O_2$+3% $N_2$, E/P ratio=25/75, total gas flow rate=175 sccm, WHSV=41 $h^{-1}$.

Example 2: Catalyst Support

BN was added to each of the following supporting materials: silicon dioxide $SiO_2$ (Amorphous, T4 Soot Corning) and mesoporous silica nanoparticulate SBA-15. The BN loading in each case was 10 wt. % ($BNSi_{3.7}O_{7.4}$). Samples were milled and then calcined according to the following procedure: heat from room temperature to 105° C. in 16 minutes, hold at 105° C. for 3 hours, heat from 105° C. to 550° C. in 1 hour and 29 minutes, hold at 550° C. for 8 hours. SBA-15 is a mesoporous silica sieve based on uniform hexagonal pores with a pore diameter of 5-15 nanometers (nm). The framework walls are about 3.1 to about 6.4 nm in thickness, which provides higher hydrothermal and mechanical stability compared to other silica materials. The internal surface area of SBA-15 is typically 400-900 square meters per gram ($m^2/g$). All catalyst samples were pressed and sieved to 20-40 mesh size (420-841 μm) prior to catalytic tests.

ODH testing was carried out using continuous flow, fixed bed quartz tube reactors (ID=10.5 mm, length=24 inches, 60.96 cm) purchased from Technical Glass Products, Inc. Gas transfer lines were heated to 250° C. before and after the reactor unit. Heat was supplied to the reactor by a two-zone furnace with a 30.48 cm (12 in.) heating length manufactured by Applied Test Systems (ATS). The temperature was monitored by a 7-point thermocouple (Omega) sheathed in Inconel and placed inside a stainless steel thermal-well secured to the outside wall of the reactor tube. The set points of zone 1 and zone 2 of the furnace were adjusted to provide a 5.08 cm (2 in.) constant temperature region for the catalyst bed. A 300 mg portion of catalyst (20-40 mesh size) was mixed with about 3 g of quartz chips (20-40 mesh size) to fill the volume of the 3.81 cm (1.5 in.) long catalyst bed. Catalyst samples were loaded and tested without undergoing any pretreatment. A 70 mg amount of quartz wool was placed on each end of the catalyst bed to hold it in place. Tests were conducted at atmospheric pressure and temperatures ranging from 500-520° C. The gas mixture used was 70% hydrocarbon (HC, with a molar composition of 25% ethane, 75% propane)+27% $O_2$+3% $N_2$. Thus, the HC/O2 ratio was typically maintained at 2.6. $N_2$ was fed in the gas mixture as the internal standard to measure the gas expansion factor ($moles_{N2out}/moles_{N2in}$). The total gas flow rate was 35 sccm (WHSV=8 $kg_{HC}/kg_{cat}/h$). The effluent composition (product mixture) was monitored by online gas chromatography (GC) (Agilent 7890A). The GC was equipped with an FID with a CP-SilicaPlot capillary column, and a TCD with a MS 5 A packed column.

Figure 4A:
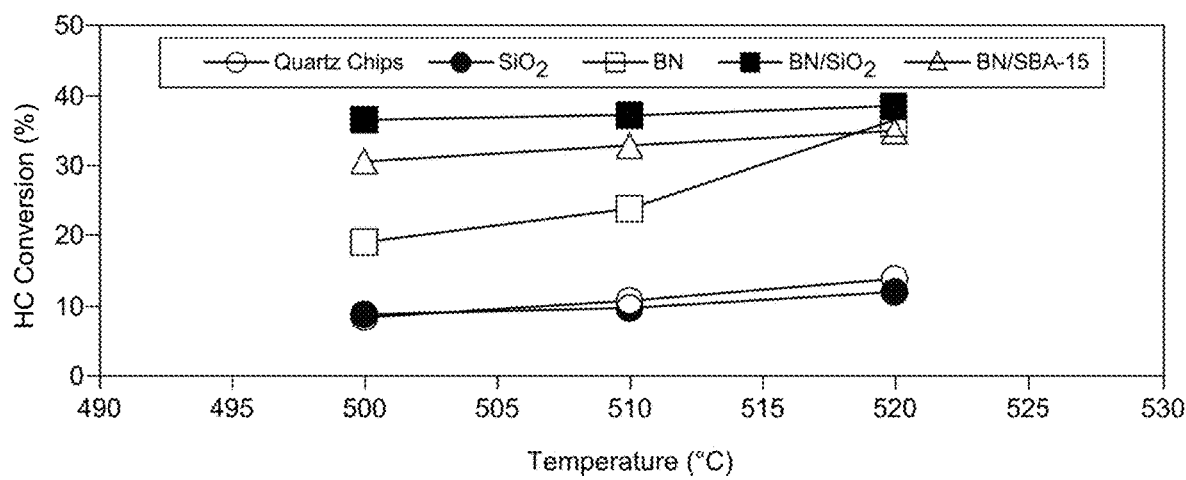
FIGS. 4A-4C show the (A) hydrocarbon conversion; (B) 02 conversion; and (C) olefin selectivity for supported catalysts according to the present disclosure.
Figure 4B:
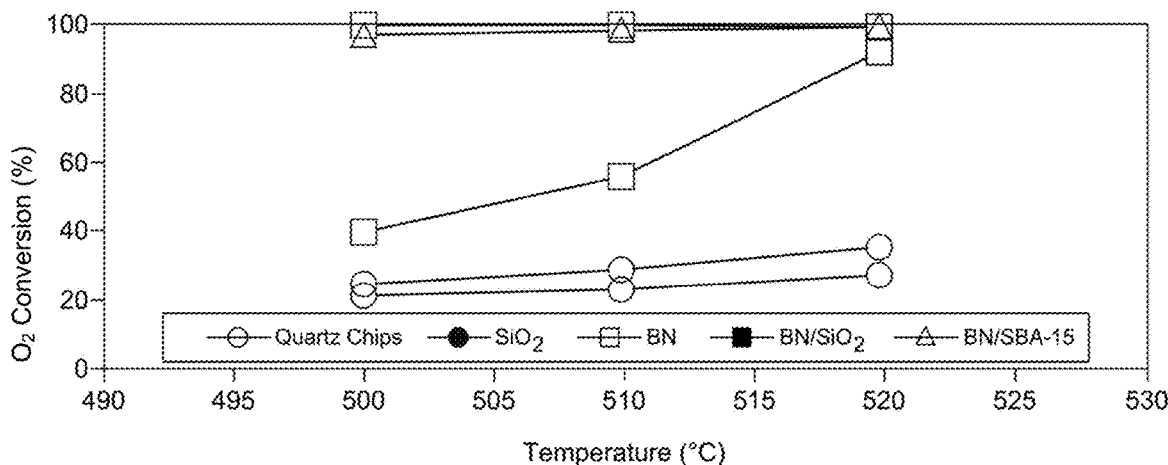
Figure 4C:
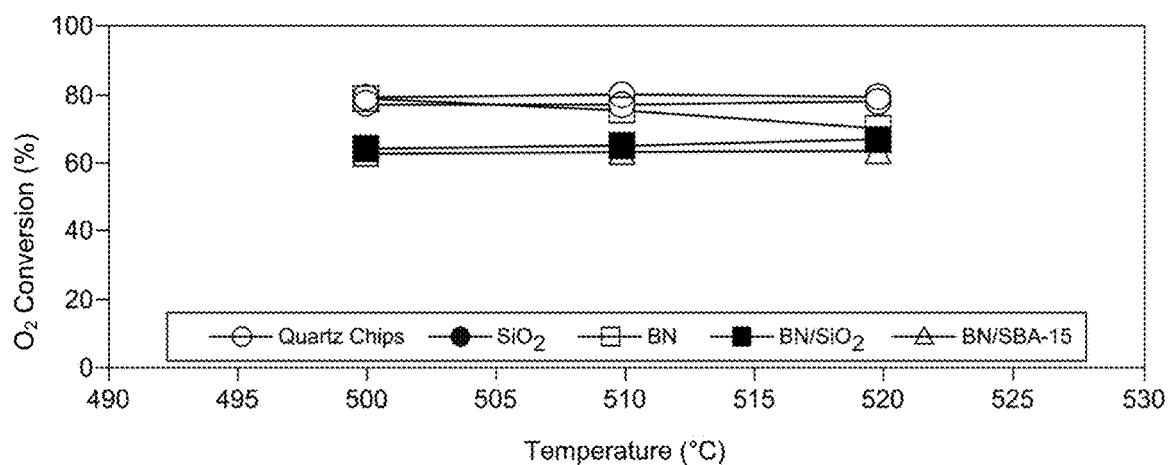

FIGS. 4A-4C present the data collected using these materials; FIG. 4A presents the hydrocarbon conversion; FIG. 4B presents the O2 conversion; FIG. 4C presents the olefin selectivity. $SiO_2$ (JAL1052) showed approximately the same activity as the quartz chips. $BN/SiO_2$ (JAL1053) and BN/SBA-15 (JAL1055) each showed significantly higher HC conversion than h-BN at 500° C. and 510° C. (about 2 times greater), and both reached 100% O2 conversion at 500° C. In contrast, h-BN did not reach 100% O2 conversion until 520° C. $BN/SiO_2$ showed slightly higher activity compared to BN/SBA-15. At 520° C., h-BN, $BN/SiO_2$, and BN/SBA-15 each exhibited approximately the same activity.

Table 2 provides the conversions and product selectivities for silica-supported BN samples at 500° C. and 510° C. as presented in FIG. 4A. Reaction conditions: gas composition=70% HC+27% $O_2$+3% $N_2$, E/P ratio=25/75, total gas flow rate=35 sccm, WHSV=8 $h^{-1}$.

TABLE 2

Conversions and product selectivities for silica-supported BN catalysts.

| Catalyst | T (° C.) | Ethane Conv. (%) | Propane Conv. (%) | HC Conv. (%) | $O_2$ Conv. (%) | Ethylene Selec. (%) | Propylene Selec. (%) | $CH_4$ Selec. (%) | CO Selec. (%) | $CO_2$ Selec. (%) | $C_{4+}$ Selec. (%) |
|---|---|---|---|---|---|---|---|---|---|---|---|
| $BN/SiO_2$ | 500 | 17 | 41 | 36 | 100 | 25 | 39 | 5 | 17 | 1 | 12 |
|  | 510 | 17 | 42 | 37 | 100 | 25 | 40 | 6 | 16 | 2 | 12 |
| BN/SBA-15 | 500 | 16 | 33 | 30 | 96 | 23 | 40 | 5 | 18 | 3 | 12 |
|  | 510 | 18 | 36 | 32 | 98 | 24 | 39 | 6 | 17 | 3 | 12 |
| h-BN | 500 | 10 | 21 | 19 | 39 | 19 | 60 | 2 | 8 | 1 | 11 |
|  | 510 | 12 | 27 | 24 | 56 | 20 | 55 | 2 | 10 | 2 | 11 |

Example 3: Effect of Functional Loading

Catalyst samples were prepared by mixing metal oxide powder with the BN powder, then milling the mixture. Subsequently, the samples were calcined in air according to the following calcination procedure: heat from room temperature to 120° C. in 19 minutes, hold for 2 hours; heat from 120° C. to 450° C. in 1 hour and 6 minutes, hold for 2 hours; heat from 450° C. to 750° C. in 1 hour, hold for 4 hours. MgO was added to h-BN with weight loadings of 9 wt. % ($BNMg_{0.06}O_{0.06}$) and 90 wt. % ($BNMg_{5.3}O_{5.3}$) based on the total weight of the catalyst. All catalyst samples were pressed and sieved to 20-40 mesh size (420-841 μm) prior to catalytic tests.

ODH testing was carried out using continuous flow, fixed bed quartz tube reactors (ID=10.5 mm, length=60.96 cm, 24 inches) purchased from Technical Glass Products, Inc. Gas transfer lines were heated to 250° C. before and after the reactor unit. Heat was supplied to the reactor by a two-zone furnace with a 30.48 cm (12 in.) heating length manufactured by Applied Test Systems (ATS). The temperature was monitored by a 7-point thermocouple (Omega) sheathed in Inconel and placed inside a stainless steel thermal-well secured to the outside wall of the reactor tube. The set points of zone 1 and zone 2 of the furnace were adjusted to provide a 5.08 cm (2 in.) constant temperature region for the catalyst bed. 300 mg of catalyst (20-40 mesh size) was mixed with about 3 g of quartz chips (20-40 mesh size) to fill the volume of the 3.81 cm (1.5 in.) long catalyst bed. Catalyst samples were loaded and tested without undergoing any pretreatment. A 70 mg amount of quartz wool was placed on each end of the catalyst bed to hold it in place. Tests were conducted at atmospheric pressure and a temperature of 550° C. The gas mixture used was 70% hydrocarbon (HC, with a molar composition of 25% ethane, 75% propane)+

27% $O_2$+3% $N_2$. Thus, the HC/$O_2$ ratio was typically maintained at 2.6. Nitrogen gas $N_2$ was fed in the gas mixture as the internal standard to measure the gas expansion factor (moles$_{N2out}$/moles$_{N2in}$). The total gas flow rate was 175 sccm (WHSV=41 kg$_{HC}$/kg$_{cat}$/h). The effluent composition (product mixture) was monitored by online gas chromatography (GC) (Agilent 7890A). The GC was equipped with an FID with a CP-SilicaPlot capillary column, and a TCD with a MS 5 A packed column.

Figure 5:
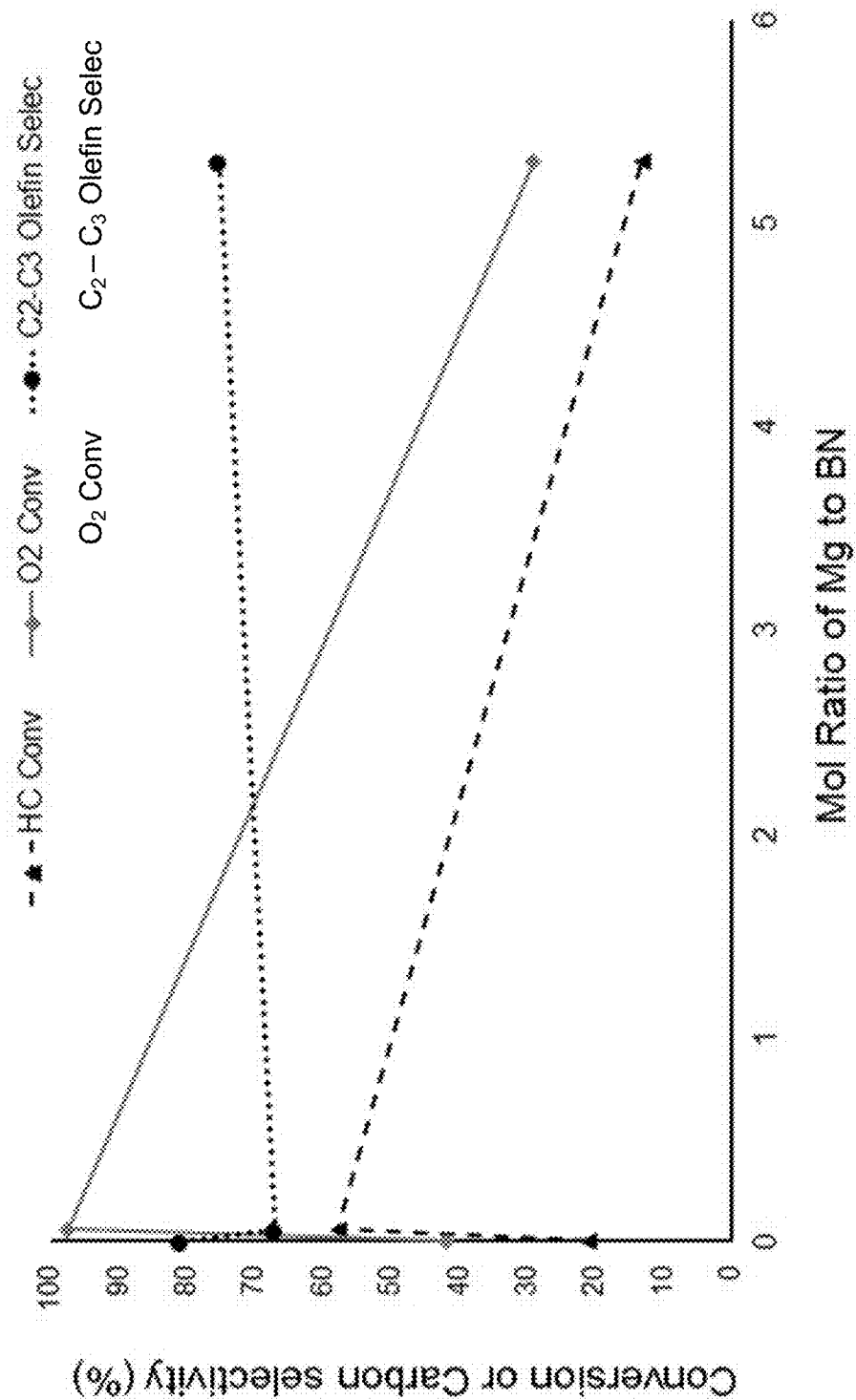
FIG. 5 presents the HC conversion, 02 conversion, and $C_2$-$C_3$ olefin selectivities at 550° C. for different loadings of MgO with Mg to BN molar ratios in the range of 0 to 5.3). Reaction conditions: gas composition=70% HC+27% $O_2$+3% $N_2$, E/P ratio=25/75, total gas flow rate=175 sccm, WHSV=41 $h^{-1}$.

FIG. 5 shows the performances of the BN, BNMg$_{0.06}$O$_{0.06}$ (9 wt % MgO), and BNMg$_{5.3}$O$_{5.3}$ (90 wt %) samples, with the conversions and selectivities plotted as a function of the MgO weight loading. A large difference in activity was observed between the samples at 550° C., with BNMg$_{0.06}$O$_{0.06}$ sample showing the highest HC conversion (58%), followed by h-BN (21%), and then BNMg$_{5.3}$O$_{5.3}$ (13%). Thus, small amounts of MgO resulted in an enhancement in catalytic activity, while higher amounts eventually led to lower activity than observed with h-BN. MgO levels of 10 wt. % or less (or Mg to BN mol ratio of less than 0.07) performed best. Table 3 provides conversions and product selectivities for silica-supported BN samples at 550° C. as shown in FIG. 5. Reaction conditions: gas composition=70% HC+27% $O_2$+3% $N_2$, E/P ratio=25/75, total gas flow rate=175 sccm, WHSV=41 h$^{-1}$.

tured by Applied Test Systems (ATS). The temperature was monitored by a 7-point thermocouple (Omega) sheathed in Inconel and placed inside a stainless steel thermal-well secured to the outside wall of the reactor tube. The set points of zone 1 and zone 2 of the furnace were adjusted to provide a 5.08 cm (2 in.) constant temperature region for the catalyst bed. A 300 mg amount of catalyst (20-40 mesh size) was mixed with about 2 g of quartz chips (20-40 mesh size) to fill the volume of the 3.81 cm (1.5 in.) long catalyst bed. Catalyst samples were loaded and tested without undergoing any pretreatment. A 70 mg amount of quartz wool was placed on each end of the catalyst bed to hold it in place. Tests were conducted at atmospheric pressure and temperatures ranging from 625-650° C. The gas mixture used was 30% hydrocarbon (HC, with a molar composition of 25% ethane, 75% propane)+10% $O_2$+60% $N_2$. Thus, the HC/02 ratio was typically maintained at 2.6. $N_2$ was fed in the gas mixture as the internal standard to measure the gas expansion factor (moles$_{N2out}$/moles$_{N2in}$). The total gas flow rate was 120 sccm. The effluent composition (product mixture) was monitored by online gas chromatography (GC) (Agilent 7890A). The GC was equipped with an FID with a CP-SilicaPlot capillary column, and a TCD with a MS 5 A packed column.

TABLE 3

Conversion and product selectivities of catalysts with varying MgO loadings

| Catalyst | Ethane Conv. (%) | Propane Conv. (%) | HC Conv. (%) | $O_2$ Conv. (%) | Ethylene Selec. (%) | Propylene Selec. (%) | $CH_4$ Selec. (%) | CO Selec. (%) | $CO_2$ Selec. (%) | $C_{4+}$ Selec. (%) |
|---|---|---|---|---|---|---|---|---|---|---|
| h-BN | 9 | 24 | 21 | 42 | 23 | 58 | 3 | 6 | 1 | 10 |
| BNMg$_{0.06}$O$_{0.06}$ (9 wt % MgO) | 29 | 65 | 58 | 98 | 40 | 27 | 11 | 11 | 1 | 10 |
| BNMg$_{5.3}$O$_{5.3}$ (90 wt % MgO) | 4 | 15 | 13 | 28 | 21 | 54 | 3 | 7 | 4 | 10 |

Example 4: Elevated Temperatures

Catalyst samples were prepared by physically mixing the MgO metal oxide powder with the BN powder, then milling the mixture. Subsequently, the samples were calcined in air according to the following calcination procedure: heat from room temperature to 120° C. in 19 minutes, hold for 2 hours; heat from 120° C. to 450° C. in 1:06 hours, hold for 2 hours; heat from 450° C. to 750° C. in 1 hour, hold for 4 hours. MgO was added in the ratio of 6 moles Mg to 100 moles BN. All catalyst samples were pressed and sieved to 20-40 mesh size (420-841 μm) prior to catalytic tests.

Figure 6A:
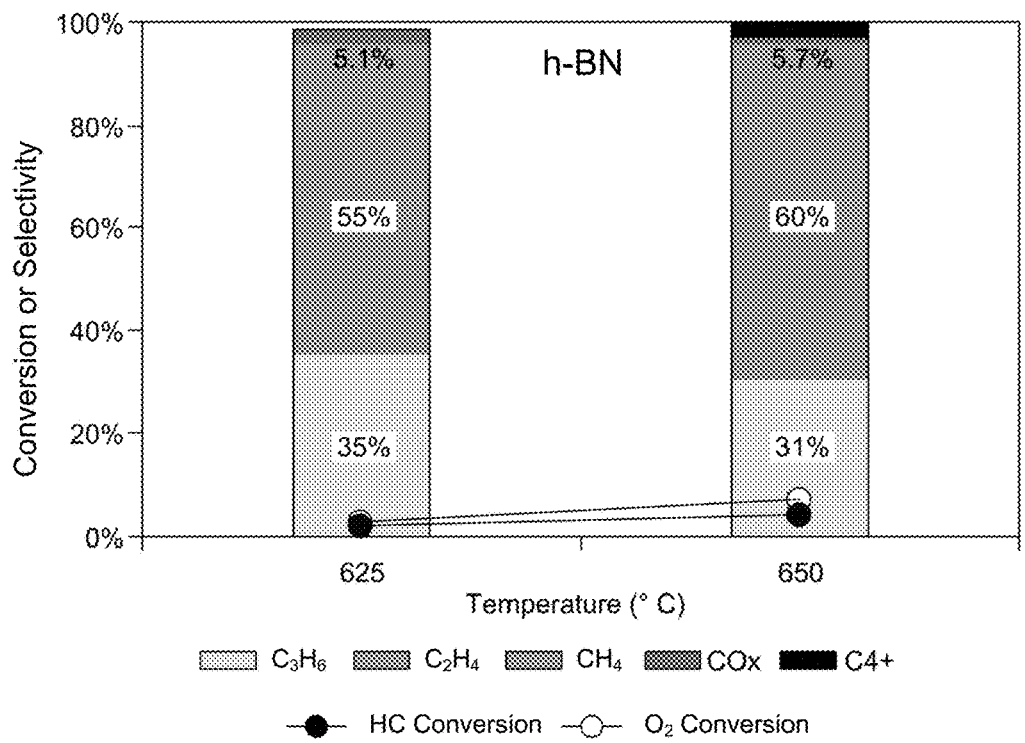
FIGS. 6A and 6B shows the conversions and selectivities for (A) h-BN μ-powder (top) and (B) $BNMg_{0.06}O_{0.06}$ μ-powder (bottom). Reaction conditions: total flow rate=120 sccm, gas composition=30% HC+10% $O_2$+60% $N_2$, E/P ratio=75/25, catalyst mass=300 mg.
Figure 6B:
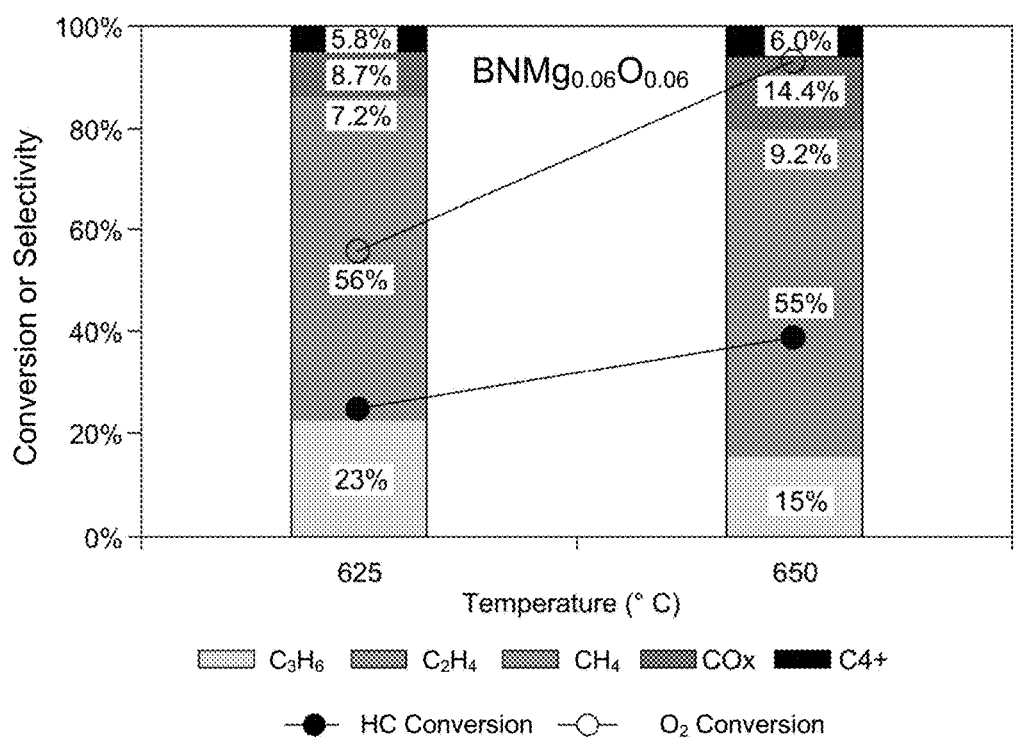

ODH testing was carried out using continuous flow, fixed bed quartz tube reactors (I.D.=7 mm, length=60.96 cm, 24 inches) purchased from Technical Glass Products, Inc. Gas transfer lines were heated to 250° C. before and after the reactor unit. Heat was supplied to the reactor by a two-zone furnace with a 30.48 cm (12 in.) heating length manufac- FIGS. 6A and 6B shows the catalytic performances of (A) h-BN (top) and (B) BNMg$_{0.06}$O$_{0.06}$ (bottom) at 625° C. and 650° C. The activity of the BN catalyst was quite low, with HC and 02 conversions only reaching 4% and 7%, respectively, at 650° C. A $C_2$-$C_3$ olefin selectivity of 91% was obtained at this low conversion. Promotion of the catalyst with MgO led to a ~10-fold increase in activity, with the HC and 02 conversions reaching 39% and 93%, respectively, at 650° C. At this high conversion, the olefin selectivity was 70%, with higher amounts of $CH_4$ and $CO_x$ produced compared to the non-promoted BN sample. This result clearly indicates a positive promotional effect that MgO has on the reactivity of the BN catalyst. Table 4 provides the conversions and selectivities on h-BN μ-powder and BNMg$_{0.06}$O$_{0.06}$ μ-powder as shown in FIGS. 6A and 6B. Reaction conditions: total flow rate=120 sccm, gas composition=30% HC+10% $O_2$+60% $N_2$, E/P ratio=75/25, catalyst mass=300 mg.

TABLE 4

Conversions and product selectivities of BN and BNMg$_{0.06}$O$_{0.06}$.

| Catalyst | T (° C.) | Ethane Conv. (%) | Propane Conv. (%) | HC Conv. (%) | $O_2$ Conv. (%) | Ethylene Selec. (%) | Propylene Selec. (%) | $CH_4$ Selec. (%) | CO Selec. (%) | $CO_2$ Selec. (%) | $C_{4+}$ Selec. (%) |
|---|---|---|---|---|---|---|---|---|---|---|---|
| h-BN | 625 | 1 | 4 | 2 | 2 | 55 | 35 | 5 | 2 | 1 | 2 |
|  | 650 | 7 | 15 | 10 | 7 | 60 | 31 | 6 | 2 | 1 | 4 |

TABLE 4-continued

Conversions and product selectivities of BN and BNMg$_{0.06}$O$_{0.06}$.

| Catalyst | T (° C.) | Ethane Conv. (%) | Propane Conv. (%) | HC Conv. (%) | O$_2$ Conv. (%) | Ethylene Selec. (%) | Propylene Selec. (%) | CH$_4$ Selec. (%) | CO Selec. (%) | CO$_2$ Selec. (%) | C$_{4+}$ Selec. (%) |
|---|---|---|---|---|---|---|---|---|---|---|---|
| BNMg$_{0.06}$O$_{0.06}$ | 625 | 20 | 37 | 25 | 56 | 56 | 23 | 7 | 8 | 1 | 6 |
| (9 wt % MgO) | 650 | 31 | 55 | 39 | 94 | 55 | 15 | 9 | 12 | 2 | 6 |

Table 5 provides the conversions and selectivities on h-BN μ-powder and BNMg$_{0.06}$O$_{0.06}$ μ-powder as shown in FIGS. 6A and 6B. Reaction conditions: total flow rate=180 sccm, gas composition=30% HC+10% O$_2$+60% N$_2$, E/P ratio=75/25, catalyst mass=300 mg.

TABLE 5

Conversions and product selectivities of BN and BNMg$_{0.06}$O$_{0.06}$.

| Catalyst | T (° C.) | Ethane Conv. (%) | Propane Conv. (%) | HC Conv. (%) | O$_2$ Conv. (%) | Ethylene Selec. (%) | Propylene Selec. (%) | CH$_4$ Selec. (%) | CO Selec. (%) | CO$_2$ Selec. (%) | C$_{4+}$ Selec. (%) |
|---|---|---|---|---|---|---|---|---|---|---|---|
| h-BN | 625 | 0 | 2 | 1 | 2 | 55 | 35 | 5 | 2 | 1 | 3 |
|  | 650 | 3 | 7 | 4 | 7 | 60 | 31 | 6 | 1 | 0 | 3 |
| BNMg$_{0.06}$O$_{0.06}$ | 625 | 10 | 20 | 14 | 29 | 59 | 28 | 7 | 1 | 0 | 5 |
| (9 wt % MgO) | 650 | 27 | 49 | 35 | 77 | 56 | 18 | 8 | 10 | 1 | 6 |

Definitions

It is also to be understood that the terminology used herein is for the purpose of describing particular aspects only and is not intended to be limiting. As used in the specification and in the claims, the term "comprising" can include the embodiments "consisting of" and "consisting essentially of" Unless defined otherwise, all technical and scientific terms used herein have the same meaning as commonly understood by one of ordinary skill in the art to which this disclosure belongs. In this specification and in the claims which follow, reference will be made to a number of terms which shall be defined herein.

As used herein, the term "combination" is inclusive of blends, mixtures, alloys, reaction products, and the like.

Ranges can be expressed herein as from one value (first value) to another value (second value). When such a range is expressed, the range includes in some aspects one or both of the first value and the second value. Similarly, when values are expressed as approximations, by use of the antecedent 'about,' it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the designated value, approximately the designated value, or about the same as the designated value. It is generally understood, as used herein, that the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not. For example, the phrase "optional additional additives" means that the additional additives can or cannot be included and that the description includes compositions that both include and do not include additional additives.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific aspect or combination of aspects of the methods of the disclosure.

References in the specification and concluding claims to parts by weight of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included. As used herein the terms "weight percent," "wt %," and "wt. %," which can be used interchangeably, indicate the percent by weight of a given component based on the total weight of the composition, unless otherwise specified. That is, unless otherwise specified, all wt % values are based on the total weight of the composition. It should be understood that the sum of wt % values for all components in a disclosed composition or formulation are equal to 100.

Unless otherwise stated to the contrary herein, all test standards are the most recent standard in effect at the time of filing this application. Each of the materials disclosed herein are either commercially available and/or the methods for the production thereof are known to those of skill in the art. It is understood that the compositions disclosed herein have certain functions. Disclosed herein are certain structural requirements for performing the disclosed functions and it is understood that there are a variety of structures that can perform the same function that are related to the disclosed structures, and that these structures will typically achieve the same result.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise. The term "about" as used herein can allow for a degree of variability in a value or range, for example, within 10%, within 5%, or within 1% of a stated value or of a stated limit of a range, and includes the exact stated value or range. The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. While "about" permits some tolerance, a person of ordinary skill in the art would read the specification in light of his knowledge and skill for guidance on the level of that tolerance, and be reasonably apprised to a reasonable degree the metes and bounds of the claims.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

An olefin is an unsaturated hydrocarbon containing at least one carbon-carbon double bond. The term "light olefin" as used herein may refer to ethylene, propylene, 1-butene, 2-butene, and isobutene.

The term "oxidative dehydrogenation" as used herein may refer to a process of endothermic dehydrogenation of ethane with the strongly exothermic oxidation of hydrogen. Oxidative dehydrogenation of alkanes. ODH of alkanes may proceed via the reaction process below. An alkane or hydrocarbon source may react with lattice oxygen to form alkenes, with a rate constant $k_1$ or $CO_x$, with a rate constant $k_2$. The alkenes formed undergo subsequent oxidation to $CO_x$ with a rate constant $k_3$. The disclosed catalysts facilitate formation of the desired olefin products.

The term "surface" as used herein refers to a boundary or side of an object, wherein the boundary or side can have any perimeter shape and can have any three-dimensional shape, including flat, curved, or angular, wherein the boundary or side can be continuous or discontinuous. While the term surface generally refers to the outermost boundary of an object with no implied depth, when the term 'pores' is used in reference to a surface, it refers to both the surface opening and the depth to which the pores extend beneath the surface into the substrate.

The term "butane" refers to all isomers of butane unless specifically stated. Butane isomers include n-butane, isobutane (methylpropane) and mixtures thereof.

The term "catalyst" means a substance that alters the rate of a chemical reaction. "Catalytic" means having the properties of a catalyst.

The term "conversion" means the mole fraction (i.e., percent) of a reactant converted to a product or products. As used herein, the term "selectivity" refers to the percent of converted reactant that went to a specified product, for example, 1-butene selectivity is the % of butane that converted to 1-butene.

As used herein, the term "about" or "approximately" are defined as being close to as understood by one of ordinary skill in the art. In one non-limiting aspect, the terms are defined to be within 10%, preferably within 5%, more preferably within 1%, and most preferably within 0.5%.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification includes any measurable decrease or complete inhibition to achieve a desired result. The term "surface" as used herein refers to a boundary or side of an object, wherein the boundary or side can have any perimeter shape and can have any three-dimensional shape, including flat, curved, or angular, wherein the boundary or side can be continuous or discontinuous. While the term surface generally refers to the outermost boundary of an object with no implied depth, when the term 'pores' is used in reference to a surface, it refers to both the surface opening and the depth to which the pores extend beneath the surface into the substrate.

All publications mentioned herein are incorporated herein by reference to disclose and describe the methods and/or materials in connection with which the publications are cited. The above description is intended to be illustrative, and not restrictive. For example, the above-described examples (or one or more aspects thereof) may be used in combination with each other. Other embodiments or aspects can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the disclosure should be determined with reference to the appended claims, along with the full scope of equivalents to which such claims are entitled.

What is claimed:

1. A catalyst comprising:
   a composition having a formula $BN_xM_yO_z$ wherein
   B represents boron, N represents nitrogen, M is platinum, silver, lanthanum, cerium, zirconium, titanium, tin, strontium, magnesium, tungsten, copper, lithium, sodium, calcium, manganese, zinc, lead, barium, gallium, yttrium, ytterbium, silicon, cesium, germanium, niobium, vanadium, chromium, molybdenum, rhenium, or a combination thereof, and O represents oxygen,
   x ranges from 0 to 1,
   y ranges from 0.01 to 5.5; and
   z ranges from 0 to 16.5.

2. The catalyst of claim 1, wherein x ranges from 0.01 to 1.

3. The catalyst of claim 1, wherein x ranges from 0.9 to 1.

4. The catalyst of claim 3, wherein y and z range from 0.01 to 0.06.

5. The catalyst of claim 4, wherein y and z are 0.06.

6. The catalyst of claim 5, wherein x is equal to 1 and boron is present as a component of boron nitride.

7. The catalyst of claim 3, wherein y and z are equal.

8. The catalyst of claim 3, wherein M and O is speciated as magnesium oxide.

9. The catalyst of claim 3, wherein M is strontium and M and O is speciated as strontium oxide.

10. The catalyst of claim 6, wherein boron nitride is present as hexagonal boron nitride.

11. The catalyst of claim 6, wherein boron nitride is present as cubic, wurtzitic, or amorphous boron nitride.

12. The catalyst of claim 3, further comprising a support.

13. The catalyst of claim 12, wherein the catalyst is suitable for converting an alkane to an olefin and wherein the olefin comprises ethylene, propylene, butylene, isobutene, or a combination thereof.

14. The catalyst of claim 13, wherein the olefin is a mixture of ethylene and propylene.

15. A method of forming a catalyst, the method comprising:
   combining one or more of elemental boron and boron nitride with one or more of (i) a metal, (ii) a metalloid, (iii) an oxide of a metal, and (iv) an oxide of a metalloid to form a mixture; and
   milling the mixture;
   calcining the milled mixture at a temperature of about 100° C. to about 800° C. for at least a first time period to provide the catalyst.

16. The method of claim 15, wherein calcining proceeds at a temperature of about 100° C. to about 800° C.

17. The method of claim 15, wherein the calcining comprises heating at about 120° C. for a first time period.

18. The method of claim 15, wherein the calcining occurs for at least a second time period.

19. The method of claim 15, wherein the milling comprises grinding the mixture to a particle size of less than 0.5 mm.

20. A method of converting alkanes to olefins, the method comprising:
   contacting a hydrocarbon source with a catalyst and an oxidant at a temperature of from about 400° C. to about 700° C.,
   wherein the catalyst comprises a composition having a formula $BN_xM_yO_z$, wherein B represents boron, N represents nitrogen, M comprises a metal or metalloid, and O represents oxygen, x ranges from 0 to 1, y ranges from 0.01 to 5.5; and z ranges from 0 to 16.5.

* * * * *